3,931,257

United States Patent [19]
Pawson

[45] Jan. 6, 1976

[54] POLYENE COMPOUNDS

[75] Inventor: Beverly Ann Pawson, Montclair, N.J.

[73] Assignee: Hoffmann-La Roche Inc., Nutley, N.J.

[22] Filed: Aug. 7, 1974

[21] Appl. No.: 495,367

[52] U.S. Cl............ 260/408; 260/243 B; 260/247.2; 260/293.72; 260/295 R; 260/326.43; 260/404; 260/410.9 R; 260/410.9 V; 260/413; 260/577; 260/578; 260/583 A; 260/606.5 P; 260/611 V; 260/613 D; 260/617 A
[51] Int. Cl.² .................. C11C 1/00; C11C 3/00
[58] Field of Search............ 260/413, 408, 410.9 R, 260/410.9 V; 424/318

[56] References Cited
UNITED STATES PATENTS

| | | |
|---|---|---|
| 2,529,498 | 11/1950 | Isler ........................... 260/617 A |
| 3,247,239 | 4/1966 | Truscheit et al. ............. 260/405.5 |
| 3,761,495 | 9/1973 | Findlay ...................... 260/410.9 R |
| 3,781,313 | 12/1973 | Julia............................ 260/410.9 V |
| 3,876,673 | 4/1975 | Julia............................ 260/413 |

Primary Examiner—Winston A. Douglas
Assistant Examiner—P. E. Konopka
Attorney, Agent, or Firm—Samuel L. Welt; Jon S. Saxe; R. Hain Swope

[57] ABSTRACT

Novel 9-substituted phenyl- or cyclohex-1-en-1-yl-3,7-dimethyl-nona-2,4,6-trienoic acids or derivatives thereof, -trienal or -trienol derivatives are described. The subject compounds are useful in the treatment of certain dermatoses and inflammatory and allergic dermatological conditions.

4 Claims, No Drawings

POLYENE COMPOUNDS

DETAILED DESCRIPTION OF THE INVENTION

The present invention pertains to compounds represented by the formula

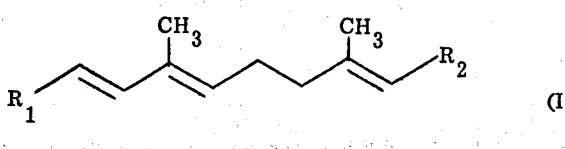

wherein $R_1$ is a 2,6,6-trimethyl-cyclohex-1-en-1-yl group or a phenyl group which is substituted in positions 2 and 6 by a member selected from the group consisting of halogen, lower alkyl and lower alkoxy and in at least one of positions 3, 4 and 5 by a member selected from the group consisting of halogen, hydroxy, lower alkyl, lower alkenyl, lower alkoxy, lower alkenoxy, lower alkanoyloxy, nitro, amino, mono(lower alkyl)amino, di(lower alkyl)amino, lower alkanoylamido and a nitrogen-containing heterocyclic group; and $R_2$ is selected from the group consisting of formyl, hydroxymethyl, alkoxymethyl, alkanoyloxymethyl, carboxyl, alkoxycarbonyl, alkenoxycarbonyl, alkynoxycarbonyl, carbamoyl, mono(lower alkyl) carbamoyl, di(lower alkyl)carbamoyl and a nitrogen-containing heterocycle-substituted carbonyl group.

The term "halogen" as utilized in the instant specification denotes all form halogens, i.e., chlorine, bromine, iodine and fluorine, with chlorine and bromine being preferred. The terms "lower alkyl" and "lower alkenyl" denote both straight- and branched-chain groups containing 1 to 6 carbon atoms such as, for example, methyl, ethyl, isopropyl and 2-methylpropyl and vinyl, allyl and butenyl, respectively. The terms "lower alkoxy" and "lower alkenoxy" denote groups containing 1 to 6 carbon atoms such as, for example, methoxy, ethoxy and isopropoxy and vinyloxy and allyloxy, respectively. The lower alkanoyloxy groups preferably contain up to 6 carbon atoms such as, for example, acetoxy, propionyloxy, butyryloxy and the like.

The amino group as represented in the above formulae may be mono- or disubstituted by lower alkyl groups containing from 1 to 6 carbon atoms such as, for example, methylamino, diethylamino and isopropylamino. The alkanoyl portion of the lower alkanoylamido groups of the above formula can be derived from lower alkanecarboxylic acids having 1 to 6 carbon atoms such as, for example, acetic acid, propionic acid, pivalic acid and the like.

The terminology "nitrogen-containing heterocycle" as utilized herein denotes a 5- or 6-membered ring containing a nitrogen atom and which may contain an additional hetero atom selected from the group consisting of oxygen, nitrogen and sulfur. Examples of preferred groups in accordance with the invention include pyrrolidino, pyridino, piperidino, morpholino and thiomorpholino. The alkoxy portion of the alkoxymethyl and alkoxycarbonyl groups are preferably straight- or branched-chain groups containing from 1 to 6 carbon atoms such as, for example, methoxy, ethoxy or isopropoxy. The alkoxy portion of said groups, however, may also contain from 7 to 20 carbon atoms. Of this group the cetyloxy group is preferred.

The alkenoxycarbonyl and alkynoxycarbonyl groups in the above formula preferably contain 2 to 6 carbon atoms in the alkenoxy and alkynoxy portions, respectively. Examples of suitable groups include alkyloxy and 2-propynyloxy. The alkanoyloxy portion of the alkanoyloxymethyl group of the above formula can be derived from lower alkanecarboxylic acids having from 1 to 20 carbons, preferably from 1 to 6 carbon atoms. Examples of suitable acids include acetic acid, propionic acid, pivalic acid, palmitic acid and stearic acid. The carbamoyl group of the above formula can be mono- or di-substituted by straight- or branched-chain lower alkyl groups. Examples of suitable preferred groups include methylcarbamoyl, dimethylcarbamoyl and diethylcarbamoyl. The nitrogen-containing heterocycle portion of the nitrogen-containing heterocycle-substituted carbonyl group is defined above.

Preferred compounds of formula I in accordance with the invention include the following:

3,7-dimethyl-9-(2,6,6-trimethyl-cyclohex-1-en-1-yl)-nona-2,6,8-trien-1-oic acid methyl ester;
3,7-dimethyl-9-(2,6,6-trimethyl-cyclohex-1-en-1-yl)-nona-2,6,8-trien-1-oic acid;
3,7-dimethyl-9-(2,6,6-trimethyl-cyclohex-1-en-1-yl)-nona-2,6,8-trien-1-ol;
1-acetoxy-3,7-dimethyl-9-(2,6,6-trimethyl-cyclohex-1-en-1-yl)-nona-2,6,8-triene;
3,7-dimethyl-9-(2,3,6-trimethyl-phenyl)-nona-2,6,8-trien-1-oic acid;
3,7-dimethyl-9-(4-methoxy-2,3,6-trimethyl-phenyl)-nona-2,6,8-trien-1-oic acid methyl ester;
3,7-dimethyl-9-(3-chloro-2,4,6-trimethyl-phenyl)-nona-2,6,8-trien-1-oic acid;
3,7-dimethyl-9-(3-nitro-2,4,6-trimethyl-phenyl)-nona-2,6,8-trien-1-oic acid;
3,7-dimethyl-9-(3-chloro-2,4,6-trimethyl-phenyl)-nona-2,6,8-trien-1-oic acid methyl ester;
3,7-dimethyl-9-(3-chloro-2,6-dimethyl-4-methoxyphenyl)-2,6,8-nonatrien-1-ol acetate;
3,7-dimethyl-9-(3-chloro-2,6-dimethyl-4-methoxyphenyl)-nona-2,6,8-trien-1-oic acid and
3,7-dimethyl-9-(3-nitro-2,4,6-trimethyl-phenyl)-2,6,8-nona-trien-1-ol acetate.

In accordance with the present invention, the novel polyene compounds of formula I are prepared by condensing a compound represented by the formula

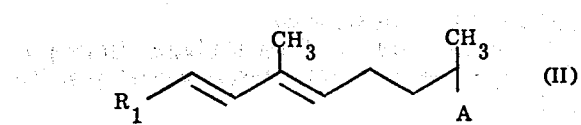

with a compound represented by the formula

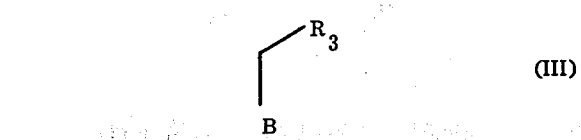

wherein one member of A and B is oxo and the other is a triarylphosphonium group represented by the formula $-P[Y]_3^+Z^-$, in which Y is an aryl group, Z is an anion of an inorganic or organic acid, $R_1$ is as given above and, wherein B is oxo, $R_3$ is selected from the group consisting of alkoxymethyl, dialkoxymethyl, alkanoyloxymethyl, alkoxycarbonyl, alkenoxycarbonyl and alkynoxycarbonyl, wherein B is triarylphosphonium, $R_3$ is selected from the group consisting of formyl, hydroxymethyl, alkoxymethyl, dialkoxymethyl, carboxyl, alkoxycarbonyl, alkenoxycarbonyl and alkynoxycarbonyl.

The novel compounds of formula I may also be prepared by reacting a compound represented by the formula

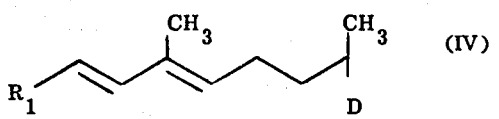

(IV)

wherein $R_1$ is as given above and D is oxo with a compound represented by the formula

(V)

wherein $R_4$ is selected from the group consisting of formyl, carboxyl, alkoxycarbonyl, alkenoxycarbonyl, alkynoxycarbonyl, carbamoyl, mono(lower alkyl)carbamoyl, di(lower alkyl) carbamoyl and a nitrogen-containing heterocycle substituted carbonyl group and E is a dialkoxyphosphinoxy group represented by the formula $$-\underset{\underset{O}{\downarrow}}{P}[X]_2$$

wherein X is an alkoxy group.

The novel compounds of formula I may also be prepared by reacting a compound represented by the formula

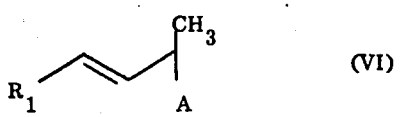

(VI)

with a compound represented by the formula

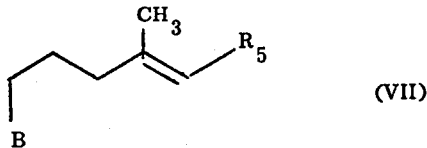

(VII)

wherein $R_1$, A and B have the meaning given above and wherein B is oxo, $R_5$ is selected from the group consisting of alkoxymethyl, dialkoxymethyl, alkanoyloxymethyl, alkoxycarbonyl, alkenoxycarbonyl and alkynoxycarbonyl, wherein B is a triarylphosphonium group, $R_5$ is selected from the group consisting of hydroxymethyl, alkoxymethyl, dialkoxymethyl, carboxyl, alkoxycarbonyl, alkenoxycarbonyl and alkynoxycarbonyl.

The novel compounds of formula I may further be prepared by reacting a compound represented by the formula

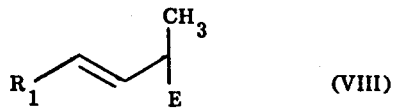

(VIII)

with a compound represented by the formula

(IX)

wherein $R_1$, D and E are as given above and $R_6$ is selected from the group consisting of alkoxymethyl, dialkoxymethyl, alkanoyloxymethyl, alkoxycarbonyl, alkenoxycarbonyl, alkynoxycarbonyl, carbamoyl, mono(lower alkyl)carbamoyl, di(lower alkyl)carbamoyl and a nitrogen-containing heterocycle-substituted carbonyl group.

Finally, the novel compounds of formula I may be prepared by reacting a compound represented by the formula

(X)

with a compound represented by the formula

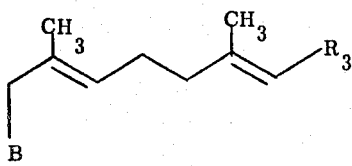

(XI)

wherein $R_1$, $R_3$, A and B have the meaning given above.

Wherein a carboxylic acid is obtained, it may be esterified or amidated. Wherein an ester is formed, it may, if desired, be hydrolyzed or amidated. Wherein either a carboxylic acid or ester are obtained, these may optionally be reduced to form the corresponding alcohol. Such alcohols may be etherified or esterified. The alcohol ester can also, if desired, be saponified. The alcohol or an ester thereof can further be oxidized to form the corresponding carboxylic acid.

The aryl groups represented by "Y" in the above formulae include all generally known aryl groups. Preferred groups include, for example, mononuclear groups such as phenyl, lower alkyl-substituted phenyl and lower alkoxysubstituted phenyl such as, for example, tolyl, xylyl, mesityl and p-methoxyphenyl. Preferred among the inorganic acid anions represented by "Z" in the above formulae are chlorine, bromide, iodide and hydrosulfate and, of the organic acid anions, the tosyloxy ion is preferred.

The alkoxy groups represented by "X" in the dialkoxyphosphinoxy group in the above formulae are preferably lower alkoxy groups containing from 1 to 6 carbon atoms. Especially preferred are methoxy and ethoxy groups.

The compounds of formula II are novel and can be prepared, for example, wherein $R_1$ is a 2,6,6-trimethyl-cyclohexenyl group and X is oxo, by condensing 1-chloro-3-methyl-5-(2,6,6-trimethyl-cyclohex-1-en-1-yl)-penta-2,4-diene by conventional procedures with ethyl acetoacetate. The resulting 3-ethoxycarbonyl-6-methyl-8-(2,6,6-trimethyl-cyclohex-1-en-1-yl)-octa-5,7-dien-2-one is then hydrolyzed and decarboxylated by conventional procedures.

The compounds of formula II wherein $R_1$ is substituted phenyl can be prepared, for example, by halogenating the corresponding 3-hydroxy-3-methyl-5-(substituted phenyl)-penta-1,4-diene under allylic rearrangement and condensing the thus-formed 1-halo-3-methyl-5-(substituted phenyl)-penta-2,4-diene in a conventional manner with ethyl acetoacetate to yield the beta-keto-carboxylic acid ester which is then conventionally hydrolyzed and decarboxylated.

Compounds of formula II wherein $R_1$ is 2,6,6-trimethyl-cyclohexenyl or a substituted-phenyl group and A is a triarylphosphonium group can be prepared, for example, by reducing an appropriate compound of formula II in which A is oxo by conventional procedure, e.g., using sodium borohydride, halogenating the resulting hydroxy compound obtained by conventional procedure, e.g., by treatment with a phosphorus trihalide or phosphorus pentahalide, and reacting the resulting halide with a triarylphosphine.

The starting materials of formula III above are known compounds.

The starting materials of formula IV wherein D is oxo are identical with the compounds of formula II wherein A is oxo and can be prepared as described above for said compounds.

The starting materials of formula V are known compounds.

The starting materials of formula VI wherein $R_1$ is a 2,6,6-trimethylcyclohexenyl group are known compounds. In contrast, the starting materials of formula VI wherein $R_1$ is a substituted-phenyl group are novel and also form part of the invention.

Compounds of formula VI wherein $R_1$ is a substituted-phenyl group and A is oxo can be prepared, for example, by first treating an appropriately substituted benzene in a conventional manner with a formylating agent in the presence of a Lewis acid and then condensing the resulting substituted benzaldehyde in a conventional manner with acetone. Compounds of formula VI wherein $R_1$ is substituted-phenyl and A is a triarylphosphonium group can be prepared, e.g., by reducing an appropriate compound of formula VI wherein A is oxo in a conventional manner using sodium borohydride, halogenating the hydroxy compound obtained, e.g., by treatment with a phosphorus trihalide or phosphorus pentahalide and reacting the resulting halide with a triarylphosphine.

The starting materials of formula VII are known compounds.

The starting materials of formula VIII wherein $R_1$ is a substituted-phenyl group are novel and also form part of the invention. They can be prepared, for example, by reacting the halide obtained in the preparation of compounds of formula VI above wherein $R_1$ is a substituted-phenyl group and A is a triarylphosphonium group with a trialkylphosphite instead of a triarylphosphine.

The starting materials of formula IX wherein D is oxo are known compounds.

In accordance with the process provided by the present invention, the reaction of compounds of formulae II and III, IV and V, VI and VII, VIII and IX or X and XI to give polyene compounds of formula I is carried out by a Wittig or Horner reaction.

According to the Wittig procedure, the starting materials are condensed together in the presence of an acid-binding agent, e.g., an alkali metal alcoholate such as sodium methylate or an alkylene oxide which may be alkyl-substituted, especially ethylene oxide or 1,2-butylene oxide. The reaction may be carried out, if desired, in a solvent, e.g., a chlorinated hydrocarbon such as methylene chloride, or dimethylformamide, at a temperature between room temperature and the boiling point of the condensation mixture.

According to the Horner procedure, the condensation is carried out with the aid of a base and preferably in the presence of an inert organic solvent such as, for example, using sodium hydride in benzene, toluene, dimethylformamide, tetrahydrofuran, dioxane or 1,2-dimethoxyethane, or using an alkali metal alcoholate in an alkanol such as sodium methylate in methanol at a temperature between 0°C. and the boiling point of the condensation mixture.

A carboxylic acid of formula I can be converted in a conventional manner, for example, by treatment with thionyl chloride into an acid chloride which can be converted into an amide by treatment with ammonia or into an ester by reaction with a suitable alkanol.

A carboxylic acid ester of formula I can be hydrolyzed to a carboxylic acid in a conventional manner such as, for example, by treatment with an alkali, preferably an aqueous-alcoholic solution of sodium hydroxide or potassium hydroxide at a temperature between room temperature and the boiling point of the mixture. The resulting carboxylic acid can then be amidated utilizing an acid halide as described above. Alternately, a carboxylic acid ester can be directly amidated as described hereinafter.

A carboxylic acid ester of formula I can be converted directly into the corresponding amide by treatment with lithium amide, preferably at room temperature.

A carboxylic acid or a carboxylic acid ester of formula I may be reduced to the corresponding alcohol in a conventional manner such as, for example, by treatment with a metal hydride or alkyl metal hydride in an inert solvent. Suitable hydrides include mixed metal hydrides such as lithium aluminum hydride and bis-[methoxy-ethylenoxy]-sodium aluminum hydride. Suitable inert solvents include, for example, ether, tetrahydrofuran and dioxane wherein lithium aluminum hydride is utilized and ether, hexane, benzene and toluene wherein diisobutyl-aluminum hydride or bis-[methyloxy-ethylenoxy]-sodium aluminum hydride are utilized.

An alcohol of formula I can be etherified with an alkyl halide such as, for example, ethyl iodide, in the presence of a base, preferably sodium hydride and in an organic solvent such as, for example, dioxane, tetrahydrofuran, 1,2-dimethoxyethane, dimethylformamide and the like, or in the presence of an alkali metal alcoholate in an alkanol and at a temperature between 0°C. and room temperature.

An alcohol of formula I can also be esterified by treatment with an alkanoyl halide or anhydride, preferably in the presence of a base such as, for example, pyridine or triethylamine at a temperature between room temperature and the boiling point of the mixture.

An alcohol ester can be saponified by conventional procedure such as previously described in connection with the carboxylic acid esters.

A diacetal of formula I can be saponified by conventional procedure such as, for example, by treatment with a proton donator in an inert solvent, e.g., hydrochloric acid in tetrahydrofuran.

An alcohol of formula I or an ester thereof can be oxidized to corresponding acid by conventional means such as, for example, silver (I) oxide and an alkali in water or an organic solvent miscible with water at a temperature between room temperature and the boiling point of the mixture.

In papilloma tests, tumors induced with dimethyl-benzanthracene and croton oil were shown to regress upon treatment with the polyene compounds of formula I. The diameter of such papillomas in mice decreased by 33% within 2 weeks upon the intraperitoneal administration of 3,7-dimethyl-9-(2,6,6-trimethyl-cyclohex-1-en-1-yl)-nona-2,6,8-trien-1-oic acid methyl ester at a dosage of 400 mg/kg/week.

The polyene compounds of formula I are further useful in the topical and systemic treatment of acne, psoriasis and other dermatoses accompanied by an increased or pathologically altered cornification and for the treatment of inflammatory and allergic dermatological conditions. The compounds of formula I can also be utilized in the treatment of conditions of the mucous membranes characterized by inflammatory, degenerative or metaplastic alterations.

The compounds of formula I may be administered enterally, parenterally or topically. The dosages will vary according to mode of administration, the condition being treated and the requirements of the patient. For oral administration, from about 5 mg. to about 200 mg. of the compounds of formula I daily in one or more dosages are contemplated. A preferred oral dosage form is capsules containing from about 10 mg. to about 100 mg. of active ingredient. For topical administration, preferred dosage forms are solutions containing the active ingredient in from 0.01% by weight to about 0.3% by weight, preferably from about 0.02% by weight to about 0.1% by weight and ointments and creams containing from about 0.5% by weight to about 5% by weight, preferably from about 0.1% by weight to about 2.0% by weight active ingredient.

The toxicity of the polyene compounds of formula I is slight. For example, as is evident from the following Table, the acute toxicity ($LD_{50}$) in mice after intraperitoneal administration in rape oil of 3,7-dimethyl-9-(2,6,6-trimethylcyclohex-1-en-1-yl)-nona-2,6,8-trien-1-oic acid methyl ester is over 4000 mg/kg.

TABLE

Acute Toxicity

| Days Past Administration | $LD_{10}$ mg/kg | $LD_{50}$ mg/kg | $LD_{90}$ mg/kg |
|---|---|---|---|
| 1 | >4000 | >4000 | >4000 |
| 10 | >4000 | >4000 | >4000 |
| 20 | >4000 | >4000 | >4000 |

Wherein, in accordance with the present invention, the compounds of formula I are administered by either enteral or parenteral modes, suitable pharmaceutical dosage forms include tablets, capsules, dragees, syrups, suspensions, solutions, suppositories and the like for enteral administration. Parenteral dosage forms may be infusions or injectable solutions which can be injected intravenously or intramuscularly. These preparations can contain other medicinally active substances as well as inert binding agents, fillers, carriers or diluents. Additional additives such as flavoring agents, preservatives, stabilizers, emulsifying agents, buffers and the like may be added in accordance with accepted practices of pharmaceutical compounding. It is preferred to incorporate into the preparations herein described one or a mixture of antioxidants recognized as being suitable for such preparations such as, for example, N-methyl-γ-tocopherol-amine, tocopherols, butylated hydroxyanisole, butylated hydroxytoluene, ethoxyquin and the like. The carriers and diluents utilized may be organic or inorganic substances such as, for example, water, gelatin, lactose, starches, magnesium stearate, talc, gum arabic, polyalkyleneglycols and the like.

For topical administration, the polyene compounds of formula I are incorporated into ointments, tinctures, creams, solutions, lotions, sprays, suspensions and the like. Ointments, creams and solutions are preferred. These pharmaceutical preparations for topical administration can be prepared by mixing the polyene compounds, as the active ingredients, with non-toxic, inert solid or liquid carriers suitable for topical treatment in accordance with accepted pharmaceutical practices.

The following examples further illustrate the invention. All temperatures are in degrees Centigrade.

EXAMPLE 1

4.6 Grams of sodium hydride were washed with low boiling petroleum ether and, after addition of 100 ml.

of anhydrous dimethoxyethane, treated dropwise with 6.5 g. of ethyl acetoacetate. The mixture was heated to boiling under reflux for 1 hour and after the dropwise addition of 120 g. of 1-chloro-3-methyl-5-(2,6,6-trimethyl-cyclohex-1-en-1-yl)-penta-2,4-diene in 40 ml. of dimethoxyethane, again heated to boiling under reflux for 12 hours. After cooling, the reaction mixture was filtered. The filtrate was diluted with ether, washed to neutrality with a saturated aqueous sodium chloride solution, dried over sodium sulfate and evaporated. 14.7 Grams of the crude 3-ethoxycarbonyl-6-methyl-8-(2,6,6-trimethyl-cyclohex-1-en-1-yl)-octa-5,7-dien-2-one obtained were taken up in 500 ml. of 70% ethanol and treated with 140 g. of potassium hydroxide. The mixture was heated to boiling under reflux for 1 hour, cooled, adjusted to pH 2 by the addition of concentrated hydrochloric acid, again heated to boiling for 30 minutes until cessation of the carbon dioxide evolution and subsequently extracted with ether. The ether extract was dried over sodium sulfate and evaporated. The remaining crude 6-methyl-8-(2,6,6-trimethylcyclohex-1-en-1-yl)-octa-5,7-dien-2-one boiled between 120° and 135°/0.1 Torr. The product was purified in a conventional manner via the semicarbazone which melted at 152°.

A total of 2.85 g. of sodium hydride was washed with low boiling petroleum ether and, after addition of 400 ml. of anhydrous tetrahydrofuran, treated dropwise with 12.15 g. of dimethoxyphosphonoacetic acid methyl ester. The mixture was heated at 40°–50° for 2 hours, then cooled to 5°–10° and after addition of 12.9 g. of the 6-methyl-8-(2,6,6-trimethyl-cyclohex-1-en-1-yl)-octa-5,7-diene-2-one formed above in 50 ml. of anhydrous tetrahydrofuran, heated to boiling for 12 hours under reflux. The resulting reaction mixture was poured onto ice and taken up in ether. The ether extract was washed to neutrality with water, dried over sodium sulfate and evaporated. The crude 3,7-dimethyl-9-(2,6,6-trimethyl-cyclohex-1-en-1-yl)-nona-2,6,8-trien-1-oic acid methyl ester remaining was purified by adsorption on silica gel and separated into the isomeric forms. The pure ester boiled at 125°/0.05 Torr.

EXAMPLE 2

A total of 12.3 g. of 3-hydroxy-3-methyl-5-(4-methoxy-2,3,6-trimethylphenyl)-penta-1,4-diene are introduced into 150 ml. of absolute ether with stirring. The solution was cooled in an inert gas to −60°, treated in the course of 5–10 minutes with 39 ml. of 10.3% ethereal hydrochloric acid and stirred for 5 minutes at −60°. The mixture was then warmed to +10° with stirring and, after 5 minutes, diluted with water and extracted twice with ether. The combined ether extracts were washed to neutrality with a saturated, aqueous sodium bicarbonate solution, dried over sodium sulfate and evaporated. The remaining crude 1-chloro-3-methyl-5-(4-methoxy-2,3,6-trimethyl-phenyl)-penta-2,4-diene was reacted as described below.

3.08 Grams of sodium hydride were washed with low boiling petroleum ether and suspended in 100 ml. of dimethoxyethane. After the dropwise addition of 8.35 g. of ethyl acetoacetate, the suspension was heated to boiling under reflux for 1 hour. The clear solution was cooled to 0°, treated dropwise over a period of 20 minutes at 0°–50° with 17 g. of 1-chloro-3-methyl-5-(4-methoxy-2,3,6-trimethyl-phenyl)-penta-2,4-diene in 60 ml. of dimethoxyethane and heated to boiling under reflux for 12 hours. After cooling, the reaction mixture was filtered. The filtrate was diluted with ether, washed to neutrality with a saturated aqueous solution of sodium chloride, dried over sodium sulfate and evaporated.

22 Grams of the crude 3-ethoxycarbonyl-6-methyl-8-(4-methoxy-2,3,6-trimethyl-phenyl)-octa-5,7-dien-2-one obtained above were dissolved in 70% ethanol. After the addition of 22 g. of potassium hydroxide, the solution was heated to boiling under reflux for 1 hour, cooled, acidified by the addition of concentrated hydrochloric acid, and again heated to boiling for 1 hour. The reaction mixture was then diluted with water and extracted with ether. The ether extract was washed successively with a saturated aqueous solution of sodium bicarbonate and sodium chloride, dried over sodium sulfate and evaporated. The remaining crude 6-methyl-8-(4-methoxy-2,3,6-trimethyl-phenyl)-octa-5,7-dien-2-one melted at 89° after recrystallization from hexane.

A total of 1.8 g. of sodium hydride was washed with low boiling petroleum ether and, after the addition of 300 ml. of absolute tetrahydrofuran, treated dropwise with 9.6 g. of diethoxyphosphono-acetic acid ethyl ester. The mixture was stirred for 30 minutes at room temperature, subsequently cooled to 5° and after adding dropwise 9 g. of 6-methyl-8-(4-methoxy-2,3,6-trimethyl-phenyl)-octa-5,7-dien-2-one in 50 ml. of absolute tetrahydrofuran, heated to boiling under reflux conditions for 12 hours. The reaction mixture obained was poured onto ice and taken up in ether. The ether extract was washed to neutrality with water, dried over sodium sulfate and evaporated. The remaining crude 3,7-dimethyl-9-(4-methoxy-2,3,6-trimethyl-phenyl)-nona-2,6,8-trien-1-oic acid ethyl ester was purified by adsorption on silica gel.

EXAMPLE 3

A total of 23.25 g. of 3-chloro-2,4,6-trimethylbenzyl-triphenylphosponium chloride and 7.1 g. of ethyl beta-formylcrotonate were combined with 25 ml. of toluene and 25 ml. of 1,2-epoxybutane and heated with stirring for 18 hours at 80°–90°. The toluene was removed on a rotary evaporator and 800 ml. of hexane was added and the mixture allowed to cool. The solid was removed by filtration and the filtrate concentrated to give 23.6 g. of crude product which was purified by chromatography on silica gel and elution with methylene chloride, to give 16.2 g. of ethyl-3-methyl-5-(3-chloro-2,4,6-trimethylphenyl)-2,4-pentadienoate, b.p. 175°/0.7 mmHg.

In a 200 ml., of 4-necked flask fitted with a thermometer, magnetic stirrer and protected by an inert atmosphere, 925 mg. of lithium aluminum hydride were suspended in 25 ml. of anhydrous ether, and the mixture cooled to 0°. A solution of 5 g. of the ethyl 3-methyl-5-(3-chloro-2,4,6-trimethylphenyl)-2,4-pentadienoate formed above in 50 ml. of anhydrous ether was added dropwise at 0°–5°. The mixture was stirred at 5° for 1 hour and then 10 ml. of ethyl acetate was added cautiously at 0°–5° followed by 50 ml. of sodium sulfate solution. The mixture was then extracted twice with ether and the combined organic phases washed with a saturated aqueous solution of sodium chloride, dried with anhydrous sodium sulfate and the solvent was removed on the rotary evaporator to give 3.8 g. of 3-methyl-5-(3-chloro-2,4,6-trimethylphenyl)-2,4-pentadien-1-ol.

To a solution of 2.6 g. of 3-methyl-5-(3-chloro-2,4,6-trimethylphenyl)-2,4-pentadien-1-ol in 18 ml. of anhydrous ether in a two-necked flask fitted with a thermometer and dropping funnel 0.155 ml. of anhydrous pyridine was added. The mixture was cooled to −20° and a solution of 1.04 g. of phosphorus tribromide in 10 ml. of anhydrous ether was added slowly over a 30 minute period. The mixture was then allowed to stir for 2 hours without cooling and was then poured onto ice and extracted three times with ether. The organic extracts were washed sequentially with saturated aqueous solutions of sodium chloride, sodium bicarbonate and sodium chloride. The dried extracts were concentrated on the rotary evaporator to give 2.4 g. of 1-bromo-3-methyl-5-(3-chloro-2,4,6-trimethylphenyl)penta-2,4-diene.

A solution of 1.0 g. of distilled ethyl acetoacetate in 5 ml. of dimethoxyethane was slowly added to a suspension of 368 mg. of sodium hydride in 5 ml. of dimethoxyethane under an inert atmosphere. The mixture was allowed to stir for 1 hour and was then added dropwise to a cooled (0°) solution of 2.4 g. of 1-bromo-3-methyl-5-(3-chloro-2,4,6-trimethylphenyl)penta-2,4-diene in 10 ml. of dimethoxyethane. After the addition was complete, the reaction mixture was heated to reflux for 8 hours, cooled and filtered through Celite. The filtrate was diluted with ether and washed to neutrality with a saturated aqueous solution of sodium chloride and dried with sodium sulfate. Evaporation of the solvent yielded 2.4 g. of 3-carboethoxy-6-methyl-8-(3-chloro-2,4,6-trimethylphenyl)-5,7-octadien-2-one, which was dissolved in 10 ml. of 70% ethanol. Thereafter, 2.2 grams of potassium hydroxide were added and the mixture was heated for 1 hour on a steam bath. The solution was allowed to cool, acidified to pH 1 with concentrated hydrochloric acid and again heated to reflux for 30 minutes to complete the decarboxylation. The reaction mixture was cooled and diluted with water and ether. The organic phase was separated and the aqueous phase extracted twice more with ether. The combined ether extracts were successively washed with saturated aqueous solutions of sodium chloride, sodium bicarbonate and sodium chloride. The dried ether solution was concentrated on a rotary evaporator to yield 2.2 g. of an oil which was chromatographed on 100 g. of silica gel. Elution with methylene chloride-hexane (1:1) afforded 500 ml. of crystalline 6-methyl-8-(3-chloro-2,4,6-trimethylphenyl)-5,7-octadien-2-one, which, after three recrystallizations from hexane, had a m.p. of 65°–67°.

A total of 53.2 mg. of sodium hydride was suspended in 5 ml. of anhydrous tetrahydrofuran under an inert gas atmosphere in a 25 ml. three-necked flask equipped with a thermometer, magnetic stirrer and reflux condenser. Then, 252 mg. of dimethoxyphosphonacetic acid methyl ester were added and the mixture heated to 60° with stirring. A solution of 300 mg. of the 6-methyl-8-(3-chloro-2,4,6-trimethyl-phenyl)-5,7-octadien-2-one formed above in 5 ml. of anhydrous tetrahydrofuran was added and the mixture refluxed for 5 hours. A further 53.2 mg. of sodium hydride and 252 mg. of dimethoxyphosphonoacetic acid methyl ester were reacted as described earlier and added to the reaction mixture, which was then heated to reflux overnight. The mixture was poured into ice-water and extracted with ether. The organic phase was washed to neutrality with a saturated sodium chloride solution and dried over sodium sulfate. There were obtained 400 mg. of crude product, which was purified by chromatography on 40 g. of silica gel. By elution with methylene chloride/hexane (1:1), there were obtained 55 mg. of 3,7-dimethyl-9-(3-chloro-2,4,6-trimethyl-phenyl)-nona-2,6,8-trien-1-oic acid methyl ester.

EXAMPLE 4

A total of 2.41 g. of 3-chloro-4-methoxy-2,6-dimethylbenzyltriphenylphosphonium chloride was added under an argon atmosphere to a suspension of 0.236 g. of sodium hydride in 10 ml. of dimethylformamide which had been cooled to 15°. After the addition was complete, the mixture was stirred at room temperature for 15 minutes. A solution of 1.05 g. of 7-formyl-3-methyl-2,6-octadien-1-ol acetate in 3 ml. of dimethylformamide was slowly added to the mixture. The mixture, which slowly became clear over a period of 1 hour, was stirred at room temperature for an additional 4 hours. The mixture was then poured onto 300 ml. of ice-water with stirring. The aqueous phase was extracted with two 150 ml. portions of ethyl acetate. The organic layer was washed to neutrality with 150 ml. of saturated sodium chloride solution and dried over anhydrous sodium sulfate. Evaporation of the solvent produced an oil, which was extracted with three 100 ml. portions of hexane and 35 ml. of a 1:1 mixture of carbon tetrachloride and hexane. The extracts were combined and concentrated under vacuum to yield 1.5 g. of an oil which is purified by chromatography on 45 g. of silica gel in hexane. Elution with 1% ethyl acetate in hexane gradually increasing to 3% ethyl acetate in hexane gave 370 ml. of 3,7-dimethyl-9-(3-chloro-2,6-dimethyl-4-methoxy-phenyl)-2,6,8-nonatrien-1-ol acetate.

EXAMPLE 5

A solution of 470 mg. of 3,7-dimethyl-9-(3-chloro-2,6-dimethyl-4-methoxyphenyl)-2,6,8-nonatrien-1-ol acetate in 5 ml. of methanol was slowly added to a mixture of 1.02 g. of silver nitrate, 0.47 g. of sodium hydroxide, 1.6 ml. of water and 4.8 ml. of methanol cooled to 20°. The mixture was stirred at room temperature for 3.5 hours and then heated to 50°–55° for 1 hour. The mixture was filtered and washed well with methanol and water. The combined filtrates were evaporated on a rotary evaporator to remove the methanol. The aqueous solution was then extracted with 150 ml. of ether. The aqueous phase was separated, 30 ml. of methylene chloride were added thereto and the mixture rendered acidic with 0.58 ml. of 85% phosphoric acid. To the resulting mixture was added 30 ml. of chloroform and the organic layer was separated, washed to neutrality with a saturated sodium chloride solution and dried over anhydrous sodium sulfate. After evaporation of the filtrate, there was obtained a yellow oil which was extracted with 200 ml. of boiling isopropyl ether. Evaporation of the isopropyl ether yielded 200 mg. of crude product in the form of a waxy solid material which is recrystallized from isopropyl ether. There was thus obtained 25 mg. of 3,7-dimethyl-9-(3-chloro-2,6-dimethyl-4-methoxy-phenyl)-nona-2,6,8-trien-1-oic acid as yellow crystals, m.p. 134°–138°.

EXAMPLE 6

A mixture of 2.37 g. of 3-nitro-2,4,6-trimethylbenzyltriphenylphosphonium chloride, 1.05 g. of 7-formyl-3-methyl-2,6-octadien-1-ol acetate, 2.5 ml. of 1,2-epoxybutane and 50 ml. of toluene was heated at 80°–85° overnight. Then, 20 ml. of chloroform were added thereto and the mixture stirred at 83° overnight. The resulting mixture was evaporated on a rotary evaporator and the residue diluted with 100 ml. of ether. The organic layer was separated, washed to neutrality with a saturated sodium chloride solution and dried over sodium sulfate. After evaporation of the filtrate, there was obtained a light-yellow oil, which solidified. This solid was extracted with 125 ml. of hexane and filtered. The filtrate was evaporated on a rotary evaporator and yielded 1.9 g. of crude product as a yellow oil. This oil was chromatographed on 50 g. of silica gel in hexane. After elution with 1% ethyl acetate in hexane, gradually increasing to 3% ethyl acetate in hexane, there was obtained 77 mg. of 3,7-dimethyl-9-(3-nitro-2,4,6-trimethyl-phenyl)-2,6,8-nonatrien-1-ol acetate.

EXAMPLE 7

Soft gelatin capsules were filled with the following composition:

| Ingredient | Amount in mg. |
|---|---|
| 3,7-dimethyl-9-(2,6,6-trimethyl-cyclohex-1-en-1-yl)-nona-2,6,8-trien-1-oic acid methyl ester | 10.0 |
| Wax mixture | 41.5 |
| Vegetable oil | 98.0 |
| Trisodium salt of ethylenediamine tetraacetic acid | 0.5 |
| | 150.0 |

EXAMPLE 8

An ointment containing 0.3% of active ingredient was prepared in a conventional manner from the following composition:

| Ingredient | Amount in Grams |
|---|---|
| 3,7-dimethyl-9-(2,6,6-trimethyl-cyclohex-1-en-1-yl)-nona-2,6,8-trien-1-oic acid methyl ester | 0.3 |
| Cetyl alcohol | 2.7 |
| Lanolin | 6.0 |
| White petroleum jelly | 15.0 |
| Distilled water q.s. ad | 100.0 |

EXAMPLE 9

A water/fat emulsion containing 0.3% of active ingredient was prepared by conventional procedures from the following composition:

| Ingredient | Amount in Grams |
|---|---|
| 3,7-dimethyl-9-(2,6,6-trimethyl-cyclohex-1-en-1-yl)-nona-2,6,8-trien-1-oic acid methyl ester | 0.3 |
| Magnesium stearate | 2.0 |
| Perhydrosqualene | 13.0 |
| Distilled water q.s. ad | 100.0 |

I claim:

1. A compound selected from compounds represented by the formula

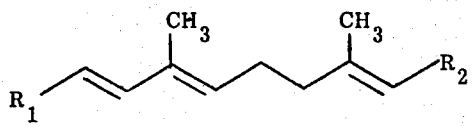

wherein $R_1$ is a 2,6,6-trimethyl-cyclohex-1-en-1-yl group or a phenyl group substituted in positions 2 and 6 by a member selected from the group consisting of halogen, lower alkyl and lower alkoxy and in at least one of positions 3, 4 and 5 by a member selected from the group consisting of halogen, hydroxy, lower alkyl, lower alkenyl, lower alkoxy, lower alkenoxy, lower alkanoyloxy and $R_2$ is carboxyl.

2. A compound in accordance with claim 1 wherein said compound is 3,7-dimethyl-9-(2,6,6-trimethyl-cyclohex-1-en-1-yl)-nona-2,6,8-trien-1-oic acid.

3. A compound in accordance with claim 1 wherein said compound is 3,7-dimethyl-9-(4-methoxy-2,3,6-trimethyl-phenyl)-nona-2,6,8-trien-1-oic acid.

4. A compound in accordance with claim 1 wherein said compound is 3,7-dimethyl-9-(3-chloro-2,6-dimethyl-4-methoxy-phenyl)-nona-2,6,8-trien-1-oic acid.

* * * * *

Disclaimer 3,931,257.—*Beverly Ann Pawson*, Montclair, N.J. POLYENE COMPOUNDS. Patent dated Jan. 6, 1976. Disclaimer filed Mar. 8, 1976, by the assignee, *Hoffmann-La Roche Inc.*

Hereby enters this disclaimer to claims 1 and 2 of said patent.

[*Official Gazette May 4, 1976.*]